United States Patent [19]

Griffiths et al.

[11] Patent Number: 5,670,132

[45] Date of Patent: Sep. 23, 1997

[54] MODIFIED RADIOANTIBODY FRAGMENTS FOR REDUCED RENAL UPTAKE

[75] Inventors: Gary L. Griffiths, Morristown; Hans J. Hansen, Mystic Island; Habibe Karacay, Matawan, all of N.J.

[73] Assignee: Immunomedics, Inc., Morris Plains, N.J.

[21] Appl. No.: 309,319

[22] Filed: Sep. 20, 1994

[51] Int. Cl.$^6$ .................. A61K 51/00; A61M 36/14
[52] U.S. Cl. ................ 424/1.11; 424/1.49; 424/1.69; 534/10; 534/14; 530/300
[58] Field of Search ................ 424/1.69, 1.11, 424/1.49, 1.65, 9.1, 78.17; 534/14, 10, 15; 530/300, 324–330, 387.1, 388.1

[56] References Cited

U.S. PATENT DOCUMENTS

| | | | |
|---|---|---|---|
| 3,927,193 | 12/1975 | Hansen et al. | 424/1.11 |
| 4,478,815 | 10/1984 | Burchiel et al. | 424/1.49 |
| 4,732,863 | 3/1988 | Tomasi et al. | 424/1.49 |
| 4,863,713 | 9/1989 | Goodwin et al. | 424/1.11 |
| 5,061,641 | 10/1991 | Shochat et al. | 534/14 |
| 5,128,119 | 7/1992 | Griffiths | 424/1.49 |
| 5,219,564 | 6/1993 | Zalipsky et al. | 424/78.17 |
| 5,277,893 | 1/1994 | Rhodes | 424/1.49 |
| 5,328,679 | 7/1994 | Hansen et al. | 424/1.49 |
| 5,334,708 | 8/1994 | Chang et al. | 530/390 |
| 5,460,785 | 10/1995 | Rhodes et al. | 424/1.49 |
| 5,514,363 | 5/1996 | Shochat et al. | 424/1.49 |

OTHER PUBLICATIONS

Wilkinson et al. "Tolerogenic Polyethylene Glycol Derivatives of Xenogeneic Monoclonal Immunoglobulins," *Immunology Letters*, 15: 17–22 (1987).

Abraham Abuchowski et al. "Effect of Covalent Attachment of Polyethylene Glycol on Immunogenicity and Circulating Life of Bovine Liver Catalase," *The Journal of Biological Chemistry*, 252: 3582–3586 (1977).

Pimm (1995) Nuclear Medicine Communications, vol. 16, pp. 710–711, "Preventing renal uptake of "In from labeled monoclonal antibody fragments.

Zimmer (1987) Cancer Research, vol. 47, Mar., pp. 1691–1694, "Pharmacokinetics of 99mTc(Sn)—and $^{131}$I labeled Anti–Carcinoembryonic Antigen Monoclonal Antibody Fragments in Nude Mice."

Tibben (1994) Nucl. Med. Biol. vol. 21, No. 1, pp. 17–24, "Decreased Kidney Uptake of Technetium–99m labeled Fab' Fragments in Ovarian Carcinoma Bearing Nude Mice Using a Cleavable Chelator."

Pimm (1994) Eur. J. Nucl. Med., vol. 21, No. 7, pp. 663–665, "Prevention of renal tubule reabsorption of radiometal Indium111" Labeled Fab fragment of a monoclonal antibody in mice by system administration of lysine.

Schott et al (1992) Cancer Research, vol. 52, No. 11, pp. 6413–6417, "Differential Metabolic Patterns of Iodinated Versus Radiometal Chelated Anticarcinoma Single Chain FV Molecules".

Sharkey et al (1990) Cancer Research, vol. 50, No. 8, pp. 2330–2336. "Biodistribution and Radiation Dose Estimates for Yttrium– and Iodine–labeled Monoclonal Antibody IgG and Fragments in Nude Mice Bearing Human Colonic Tumor Xenografts".

Griffiths et al (1994), Cancer, vol. 73, pp. 761–768, "Technetium–99m, Rhenium–186, and Rhenium–188 Direct Label Antibodies".

Kitamura, et al. "Chemical Engineering Of The Monoclonal Antibody A7 By Polyethylene Glycol For Targeting Cancer Chemotherapy," *Cancer Research* 51: 4310–15 (Aug. 15, 1991).

Griffiths et al (May 1994), Nucl. Med. Biol., vol. 21, No. 4, pp. 649–655, "Preparation of a Pure 99mTC–F(ab')2 Radioimmunoconjugate by Direct Labeling Methods".

Behr et al (1995), Cancer Research, vol. 55 pp. 3825–3834 "Reduction of the Renal Uptake of Radiolabeled Monoclonal Antibody Fragments by cationic amino acids and their derivatives".

Griffiths et al (1992). Bioconjugate Chemistry, vol. 3, No. 2, pp. 91–99, "Radiolabeling of Monoclonal Antibodies and Fragments with Technetium and Rhenium".

Griffiths et al (1994); Cancer vol. 73, No. 3, pp. 761–768 "Technetium–99m, Rhenium–186, and Rhenium–188 Direct–Labeled Antibodies".

*Primary Examiner*—John Kight
*Assistant Examiner*—Dameron L. Jones
*Attorney, Agent, or Firm*—Foley & Lardner

[57] ABSTRACT

PEG-modified-Tc-99m-radiolabeled antibody fragments are useful for radioimmunodetection of tumors and infectious lesions and display striking reductions in renal uptake and retention of radioisotope compared to non-PEG-modified fragments.

16 Claims, No Drawings

MODIFIED RADIOANTIBODY FRAGMENTS FOR REDUCED RENAL UPTAKE

BACKGROUND OF THE INVENTION

This invention relates to a method for reducing renal uptake of monoclonal antibody fragments used for radioimmunodiagnosis (RAID). Numerous clinical studies have demonstrated the utility of radiolabeled antibodies for the radioimmunodetection of disease. Preferred agents in this field are antibodies labeled with the technetium-99m isotope, which is readily available to all nuclear medicine departments, is inexpensive, gives minimal patient radiation doses, and has ideal nuclear imaging properties. The 6 h half-life of technetium-99m is most suited to application with antibody fragments, such as Fab', Fab, F(ab')$_2$ and F(ab)$_2$, which have faster targeting kinetics than intact immunoglobulin. Other advantages of fragments include a much lower occurrence of human immune responses compared to intact IgG molecules.

A preferred format for radioimmunodetection agents is the use of antibody fragments direct-labeled with technetium-99m wherein fragments containing thiol groups generated by reduction of intrinsic disulfide bonds may be quantitatively labeled with Tc-99m by the addition of sodium pertechnetate to a vial containing protein and a reductant for the pertechnetate. Other methods of producing Tc-99m radiolabeled fragments may also be useful, including a method recently disclosed which describes the use of a novel protein thiolation agent. See, for example, U.S. patent application Ser. No. 08/253,772.

A major drawback to the use of Tc-99m-labeled fragments for imaging is the relatively high uptake and retention of radioactivity in the kidney, which leads to imaging difficulties in the area of this organ. It is apparent, therefore that a method that reduces renal retention of radiolabeled antibody fragments is greatly to be desired.

SUMMARY OF THE INVENTION

It is therefore an object of the present invention to provide a method for preparing Tc-99m labeled antibody fragments which exhibit greatly reduced renal uptake and retention.

It is an additional object of the invention to provide a method for preparing an imaging agent precursor for eventual labeling with Tc-99m which exhibits greatly reduced renal uptake and retention.

These and other objects of the invention are achieved, inter alia, by providing, in a method of imaging a tumor or infectious lesion, wherein a Tc-99m-radiolabeled antibody fragment that specifically binds a marker produced by or associated with a tumor or infectious lesion is injected parenterally into a patient having a tumor or infectious lesion, and the site or sites of tumor or infectious lesion are detected by gamma camera imaging, the improvement wherein the radiolabeled antibody fragment is conjugated to an amount of polyethylene glycol (PEG) sufficient to significantly reduce renal uptake and retention of the radiolabel compared to non-PEGylated antibody fragment.

The invention further provides a method of preparing an imaging agent precursor for eventual labeling with Tc-99m radioisotope.

DETAILED DESCRIPTION

Antibody fragments which recognize antigens associated with a tumor or infectious lesion are conjugated with polyethylene glycol (PEG) and are then further modified to allow radiolabeling with technetium-99m. Antibody immunoreactivity is not affected and the PEG-fragments can be stably formulated to allow future technetium radiolabeling. The PEG-modified-Tc-99m-radiolabeled fragments are useful for immunodiagnosis and display striking reductions in renal uptake of radio isotope compared to the non-PEG-modified fragments.

As used herein, a "significant" reduction in renal uptake and retention of radioisotope means a reduction at the time of imaging by at least a factor of 2, preferably a factor of 3, more preferably a factor of 4, 6, 8, 10 or greater, relative to non-PEGylated antibody fragment at the same imaging time. Another measure of "significant" reduction in renal uptake and retention of radioisotope is the ability to clearly detect and image a tumor or infectious lesion that is otherwise obscured by high background radiation in the vicinity of the kidney when non-PEGylated antibody fragment is used, especially at short imaging times of, e.g. 1–5 hours. In general, the reduction will be most pronounced at short imaging times, affording real advantages to the clinician.

Technetium-99m has a half-life of six hours which means that rapid targeting of a technetium-labeled antibody is desirable. Antibody fragments such as F(ab')$_2$ and F(ab)$_2$, and especially Fab, Fab', show more rapid targeting kinetics than whole immunoglobulin, and are also associated with a much lower incidence of human anti-murine antibody (HAMA) immune responses. Therefore, they are preferred for RAID applications with Tc-99m labeling.

Previous workers have conjugated polyethylene glycol polymers to proteins and shown that this both reduces the immunogenicity of the proteins and enhances their circulatory lifetimes in the blood. For example, conjugation of PEG to two human monoclonal antibodies caused a marked reduction in their immunogenicity in mice, and also induced a tolerance in the same mice to challenge with the native human antibodies. Wilkinson et al., *Immunol. Lett.* 15:17 (1987). In another example, when catalase was linked to PEG-5000 the resultant conjugate retained 95% of the enzymatic activity of native catalase, but did not induce a significant immune response when injected into mice. Furthermore, the PEG-conjugated catalase remained fully active in the bloodstream of the mice 52 hours post-injection, whereas native catalase activity was reduced to background levels within 10 hours post-injection. Abuchowski et al., *J. Biol. Chem.* 252:3582 (1977).

Since antibody fragments do not engender a problematic HAMA response and target rapidly, there would not normally be a need to PEGylate such fragments for imaging. The present inventors have discovered that conjugation of PEG to Tc-99m-labeled antibody fragments causes a pronounced decrease in the amount of renal uptake and retention of the fragments. While it is known that PEG conjugation ("PEGylation") to proteins can prolong serum half-life, it was surprising and unexpected that renal uptake and retention could be dramatically reduced by PEGylation of F(ab)$_2$, F(ab')$_2$, Fab and Fab' antibody fragments that normally clear to the kidney and often obscure images of tumor or infection in the vicinity of that organ. This provides the hitherto lacking motivation to modify antibody fragments with PEG for imaging with a Tc-99m-label.

A. Preparation and PEG conjugation of antibody fragments.

The term "antibody fragment" as used herein means a molecule which specifically binds to a complementary antigen and which is derived from a whole immunoglobulin by cleavage, by recombinant methods or by any other process that results in a functional equivalent of a conventional antibody fragment. Examples of suitable antibody fragments include divalent fragments, e.g., F(ab)$_2$, F(ab')$_2$, monovalent fragments, e.g., Fab, Fab', Fv, single chain recombinant forms of the foregoing, and the like. Certain natural antibodies have carbohydrate on other than their Fc region, e.g., consensus glycosylation acceptor sequences have been identified in approximately 15–25% of murine variable regions. Kabat et al. SEQUENCES OF PROTEINS OF IMMUNOLOGICAL INTEREST, 5th ed. U.S. Department of Health and Human Services (1990). Alternatively, recombinant DNA techniques can be used to introduce carbohydrate to, e.g., the light chain of an antibody fragment.

PEG preparations with a wide variety of average molecular weights can be prepared and used for this invention. Suitable PEGs have average molecular weights of, for example, 1,000–30,000. In a preferred embodiment, a PEG with an average molecular weight of 5000 is used. PEGs suitable for the practice of the invention are commercially available from, for example, Aldrich (Milwaukee, Wis.) and Shearwater Polymers (Huntsville, Ala.).

PEGylation of antibody fragments can be achieved via methods which link the PEG either non-site-specifically to lysine residues distributed throughout the fragment, or site-specifically to sites such as a light chain carbohydrate moiety or a thiol group in the hinge region of the molecule.

To conjugate PEG in a non-site-specific fashion to lysine residues within an antibody fragment an active ester derivative of PEG may be used. Suitable active ester derivatives include pentafluorophenol, N-hydroxybenzotriazole, and N-hydroxysuccinimide (NHS) esters. In a preferred embodiment a carbonate is used, which results in a urethane bond between PEG and the protein. PEG-succinimidyl carbonate (PEG-SC) can be prepared by reaction of PEG with an excess of N,N'-disuccinimidyl carbonate, or can be purchased from Shearwater Polymers, Inc. (Huntsville, Ala.). To couple the PEG-SC to the lysine residues of an antibody fragment an excess of the PEG-SC is mixed with the fragment in aqueous buffer at a pH between approximately 7 and approximately 9. The reaction is allowed to proceed for between 0.5 and 18 hours. The reaction temperature is between approximately 4° C. and 25° C. In a preferred embodiment, the Ph is maintained at approximately 8.4, the temperature is 25° C. and the reaction time is 30 minutes. The amount of PEG which will couple to the antibody will be limited by the number of lysine residues available to react with the carbonate and the excess of PEG-SC used, as well as by the need to retain the antigen-binding capability of the antibody.

Generally, about 2–20, preferably about 4–10 PEG-5,000 moieties are desired for divalent fragments and about half that amount for monovalent fragments, with the number being smaller for higher molecular weight PEGs. In a preferred embodiment, a 6 to 10-fold excess of PEG-SC is used for PEGylation of divalent fragments. This will normally result in PEGylation of 4–10 lysines, which will translate to 2–5 PEG groups per monovalent fragment when the divalent fragment is cleaved. The number of available lysine residues which are modified can be determined by quantitation with fluorescamine. The PEG-antibody conjugate can then be purified by size-exclusion chromatography, for example, by HPLC on a BioSil 400 column (BioRad, Hercules, Calif.).

To prepare antibody fragments which are site-specifically PEGylated on thiol groups, but which retain disulfide bonds which can be used, after reduction, to bind Tc-99m, it is advantageous to use intact immuno-globulin as the starting material. The intact immuno-globulin is first partially reduced under mild conditions to produce free thiol groups, which are then reacted with a PEG derivative capable of selective reaction with thiols. Suitable PEG derivatives for this reaction include α-halo carbonyl, α-halo carboxyl, disulfides and maleimide groups. Methods of making and using these derivatives are well known to those of ordinary skill in the art. Thiol-selective activated-PEG derivatives are also commercially available, for example from Shearwater Polymers (Huntsville, Ala.). The PEG-antibody conjugate is then purified by size-exclusion chromatography and proteolytically cleaved by standard methods with pepsin to produce F(ab')$_2$ fragments, or papain to produce F(ab)$_2$ fragments.

Site-specific conjugation of PEG to antibody fragments is also possible when the fragment bears a carbohydrate residue. Intact immunoglobulins are glycosylated in the Fc region and these glycosylation sites may conveniently be used for conjugation reactions. Antibody fragments such as F(ab')$_2$ all lack the Fc portion however and thus this carbohydrate is unavailable for coupling. Some antibodies are glycosylated within the variable region and this carbohydrate is therefore retained in the corresponding fragments. In such cases the carbohydrate moiety can be oxidized with periodate and coupled with a PEG derivative bearing a nucleophilic amine residue by methods well known in the art. For example, PEG hydrazide (Shearwater Polymers, Inc., Huntsville, Ala.) is mixed with the antibody fragment to form a hydrazone. Alternatively a PEG-amine can be reacted with the oxidized carbohydrate to form a Schiff's base which is then reduced by treatment with sodium cyanoborohydride to form a stable secondary amine linkage. Alternatively, when the antibody fragment to be used does not naturally possess a light chain carbohydrate, the DNA encoding the antibody can be cloned and mutated to produce a recombinant antibody fragment including a variable region light chain carbohydrate moiety, as described in U.S. patent application Ser. No. 08/169,912, which is hereby incorporated by reference in its entirety.

For all the methods of conjugation, it is advantageous to verify that the conjugate retains the binding activity of the non-conjugated fragment. Methods for determining immunoreactivity are well known in the art. For example, conjugated antibody fragment can be passed through a column to which antigen has been bound, under conditions in which 100% of unconjugated fragment is retained. The amounts of retained and non-retained antibody are measured and compared.

B. Reduction or Derivatization of PEG-Antibody Fragments and Technetium labeling.

Once the antibody fragment has been conjugated to PEG it must be reduced or otherwise derivatized in order to produce free thiol groups suitable for direct labeling with Tc-99m. Methods for the controlled reduction of antibody fragments are well known to those of ordinary skill in the art. See, for example, U.S. Pat. No. 5,128,119 which is hereby incorporated by reference in its entirety. The disulfide bonds in the hinge region of antibody fragments are generally more accessible to disulfide reducing agents, and can normally be selectively cleaved. Provided that the reduction is performed under carefully controlled conditions, the reduced fragments retain their immunospecificity and ability to bind to antigen. Reduction of an antibody fragment with known disulfide bond reducing agents, for example dithiothreitol, cysteine, mercaptoethanol and the like, produces after a short time, typically less than one hour, fragments having at least one free sulfhydryl group. It should be noted that if reducing conditions are too drastic, or the reducing agent is left in contact with the fragments for too long, the normally less reactive disulfide bonds linking light and heavy chains will eventually be reduced, with deleterious effects on the binding properties of the antibody.

Reduction of F(ab')$_2$ and F(ab)$_2$ fragments will preferentially cleave the disulfide bonds holding together the two halves of the bivalent fragment and hence produces Fab' and Fab fragments respectively, each bearing free thiol groups.

If it is desired to image with bivalent F(ab')$_2$ and F(ab)$_2$ fragments, it will be necessary either to partially reduce interchain disulfide bonds without further cleaving the fragment or to thiolate the fragment by introduction of ligands containing thiol groups by conventional procedures, either non-site specifically or on a carbohydrate moiety, preferably one which has been engineered onto a light chain constant region of the fragment.

Once reduced, the antibody-SH moieties are quite stable if stored under rigorously oxygen-free conditions. Stability also is increased with storage at lower Ph, particularly below Ph 6. It has been found that rapid cooling to the temperature of liquid nitrogen of antibody fragments containing free thiol groups permits their storage for prolonged periods of time without deterioration or significant loss of thiol groups. It is believed that bathing the tubes containing the fragment-SH in an inert gas atmosphere, e.g. argon or nitrogen, adds to the protection of low temperature and effectively prevents reoxidation of thiol groups to disulfides.

Stabilization of the free thiol groups can also be achieved by admixing the conjugate with the agent to be used for reducing the technetium. In a preferred embodiment the added reducing agent is a tin$^{II}$ salt. The salt can be generated as required from tin metal, e.g., foil, granules, powder, turnings and the like, by contact with aqueous acid, e.g., HCl. This is usually added in the form of SnCl$_2$, advantageously in a solution that is about 0.1 mM in HCl, to a solution of a chelating ligand for stannous ion, e.g., tartrate, glucoheptonate, glucarate, and the like, to keep the Sn$^{II}$ in solution at physio-logical pH. The stannous solution is then added to the antibody. The resulting mixture can be stored as a frozen solution, or preferably is stored as a lyophilized powder. Storage of the conjugate in the presence of a reducing agent in this form is advantageous because it not only prevents reoxidation of the thiol functions, but also dispenses with the requirement of an additional step to reduce the radionuclide, as discussed below.

The PEG conjugate-reducing agent mixture can be assembled into a single vial or kit for Tc-99m labeling. Tc-99m then can be added to the kit as needed to provide a radiolabeled antibody fragment. The single vials or kits of the present invention are designed to contain the appropriate antibody fragment for any particular immuno-diagnostic procedure. The vials or kits advantageously are sealed and provided with a mechanism of introducing or withdrawing reagents under sterile conditions. Preferably, a vial containing a port for syringe injection is used in the present method. The reagents in the vials or kits typically are provided in aqueous, frozen or lyophilized form. In one embodiment the reagents can be stored at low temperature, e.g., in the refrigerator, for several days to several weeks, preferably at a pH of about 3.5–5.5, more preferably at pH 4.5–5.0, advantageously under an inert gas atmosphere, e.g., nitrogen or argon.

It also is within the scope of the present invention to provide the reagents in lyophilized form for ease of storage and stabilization. This is advantageously effected at a pH of about 5.5, from a solution of a buffer, e.g., sodium acetate, and preferably also in the presence of a stabilizer to prevent aggregation, e.g., a sugar such as trehalose or sucrose. Such lyophilization conditions are conventional and well known to one of ordinary skill in the art.

Tc-99m labeling then can be performed simply by adding the radioisotope directly from the generator e.g., in the form of aqueous sodium pertechnetate, to the mixture of the reducing agent and the reduced PEG-antibody-conjugate. The reactants are mixed and incubated for a time sufficient to effect labeling of the antibody fragment. The duration and condition of incubation are not crucial, but incubation typically is carried out for a period of time sufficient to obtain quantitative binding of Tc-99m to the antibody fragment.

In general, it is advantageous to work with a concentration of PEG conjugate of about 0.01–10 mg per ml, preferably about 0.1–5 mg/ml, of solution, generally in saline, preferably buffered to a mildly acidic pH of about 4.0–4.5. In such a case, the amount of stannous ion needed for reduction of a normal imaging activity of pertechnetate is about 0.1–50 µg/ml, preferably about 0.5–25 µg/ml, in proportion to the amount of protein. When labeling the foregoing quantity of protein, the amount of pertechnetate is generally about 2–50 mCi/mg of protein, and the time of reaction is about 0.1–10 minutes. With the preferred concentrations of protein and stannous ions, the amount of pertechnetate is preferably about 5–30 mCi/mg, and the time of reaction is preferably about 1–5 minutes.

Pertechnetate generally is obtained from a commercially available generator, most commonly in the form of NaTcO$_4$ in a saline solution. Other forms of pertechnetate may be used, with appropriate modification of the procedure, as would be suggested by the supplier of a new form of generator or as would be apparent to the ordinarily skilled practitioner. Pertechnetate is generally used at an activity of about 0.2–10 mCi/ml in saline, e.g., 0.9% ("physiological") saline, buffered at a pH of about 3–7, preferably at about 4.5–5.0. Suitable buffers include, e.g., acetate, tartrate, citrate, phosphate and the like. The reduction of pertechnetate normally is conducted under an inert gas atmosphere, e.g., nitrogen or argon. The reaction temperature is generally maintained at about room temperature, e.g., 18°–25° C.

C. Administration of Radiolabeled PEG-Antibody Fragments for Diagnosis.

Generally, the dosage of administered labeled PEG conjugate will vary depending upon such factors as the patient's age, weight, height, sex, general medical condition, and previous medical history. Typically, it is desirable to provide the recipient with a dosage of protein which is in the range of from about 1 pg/kg to 10 mg/kg (amount of agent/body weight of patient), although a lower or higher dosage may also be administered. For example, many studies have demonstrated successful diagnostic imaging with doses of 0.1 to 1.0 milligram, while other studies have shown improved localization with doses in excess of 10 milligrams. Brown, "Clinical Use of Monoclonal Antibodies," in BIO-TECHNOLOGY AND PHARMACY, Pezzuto et al., eds. Chapman & Hall, pp.227–249 (1993).

Administration of radiolabeled proteins to a patient can be intravenous, intraarterial, intraperitoneal, intramuscular, subcutaneous, intrapleural, intrathecal, by perfusion through a regional catheter, or by direct intralesional injection. Administration by injection may be by continuous infusion, or by single or multiple boluses.

The radiolabeled PEG conjugates of the present invention can be formulated according to known methods to prepare pharmaceutically useful compositions, whereby they are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 18th Ed. (1990).

The present invention, thus generally described, will be understood more readily by reference to the following examples, which are provided by way of illustration and are not intended to be limiting of the present invention.

EXAMPLES

Example 1

Preparation of PEG-modified fragments by conjugation to lysine.

IMMU-14 is a monoclonal antibody which recognizes carcinoembryonic antigen (CEA), a cell surface protein expressed in many tumors. A F(ab)$_2$ fragment of IMMU-14 was prepared by papain cleavage using standard methods.

IMMU-14F(ab)$_2$ (2.16 mg, 2.16×10$^{-8}$ mol) in 150 µl of 0.1M sodium phosphate was mixed with 10, 8, 6, 4, 2 fold molar excesses of the succinimidyl carbonate derivative of methoxy-PEG (methoxy-SC-PEG, MW 5000, Shearwater Polymers, Inc., Huntsville, Ala.) at pH 7.5, and incubated at 4° C. for 18 hours. The PEG-modified conjugates were purified by centrifuged spin columns using Sephadex G-50-80 (Pharmacia, Piscataway, N.J.) eluted with 0.1M sodium phosphate, pH 7. The conjugates were analyzed using a BioSil 400 size-exclusion HPLC column (BioRad, Hercules, Calif.). Depending on the reactant ratios, different shifts in retention times on the column were observed for the various PEG conjugates as shown in Table 1 below:

Table 1

Initial molar ratios and retention times of the conjugates on a size-exclusion HPLC BioSil 400 column eluted with 0.2M sodium phosphate, 0.02% sodium azide, pH 6.8 at 1 ml/min and detected by UV absorption at 280 nm.

TABLE 1

Initial molar ratios and retention times of the conjugates on a size-exclusion HPLC BioSil 400 column eluted with 0.2M sodium phosphate, 0.02% sodium azide, pH 6.8 at 1 ml/min and detected by UV absorption at 280 nm.

| SC-PEG: F(ab)$_2$ (reaction ratio) | retention time, min IMMU-14-F(ab')$_2$ |
|---|---|
| 10 | 8.19 |
| 8 | 8.60 |
| 6 | 8.79 |
| 4 | 9.09 |
| 2 | 9.69, 9.44 |
| 0 | 10.17 [Native IMMU-14 F(ab')$_2$] |

As expected, polymeric conjugates of the (PEG)-IMMU-14 F(ab)$_2$ were shown to be heterogeneous by SDS-PAGE analyses. PEG-IMMU-14 F(ab)$_2$ prepared by reaction with 10 equivalents of PEG was shown to have 22.5% of available lysine residues (8.5 lysine residues) modified by PEG, by fluorescamine analysis, and was referred to as PEG$_{8.5}$-IMMU-14-F(ab)$_2$.

Example 2

Reduction of PEG$_{8.5}$-IMMU-14-F(ab)$_2$ to PEG$_{4.25}$-IMMU-14-Fab.

PEG$_{4.25}$-IMMU-14-Fab-SH was obtained by reduction of PEG$_{8.5}$-IMMU-14-F(ab)$_2$ with cysteine at the hinge disulfide bonds under similar conditions to those used for unmodified F(ab)$_2$F(ab)$_2$ (15 mg/ml) was reduced in a solution of 20 mM cysteine, 2 mM EDTA, 40 mM PBS at pH 6.6 for 60 min at 37° C. Reduction of PEG$_{8.5}$-IMMU-14-F(ab)$_2$ resulted in PEG$_{4.25}$-IMMU-14-Fab-SH, which appeared as a broad peak with two unresolved shoulders on size-exclusion HPLC and SDS-PAGE, the result of varying degrees of conjugation of PEG to the antibody fragment. The retention time of PEG$_{4.25}$-Fab-SH by HPLC was 9.34, with shoulders at 9.67 and 10.08 minutes. There was no evidence of unmodified Fab (retention time 10.68 minutes).

Example 3

Formulation of PEG$_{4.25}$-IMMU-14-Fab for Tc-99m radiolabeling.

PEG$_{4.25}$-IMMU-14-Fab was formulated in 200 µg aliquots together with 38 µg of stannous ion and a 35 molar excess of sodium tartrate to Sn(II) ion per vial. Vials were frozen in dry ice and lyophilized overnight. The stability of the lyophilized vials of PEG$_{4.25}$-IMMU-14-Fab-SH was compared with non-lyophilized samples by HPLC and SDS-PAGE analyses after reconstitution with saline. No differences were observed between the freshly prepared and the lyophilized samples, demonstrating the stability of the PEG-antibody linkage under the lyophilization conditions.

Example 4

$^{99m}$Tc Labeling of PEG$_{4.25}$-IMMU-14-Fab.

$^{99m}$Tc labeling was performed by reconstituting lyophilized vials prepared as in Example 3 with 1 ml of Na$^{99m}$TcO$_4$(1–4 mCi) in saline purged with argon. The labeling was monitored by size-exclusion HPLC and instant thin-layer chromatography (ITLC). The immunoreactivity of the $^{99m}$Tc labeled IMMU-14-Fab fragment was determined by an HPLC method. An 80x molar excess of CEA was mixed with the $^{99m}$Tc labeled product and the mixture analyzed by HPLC. The HPLC peak corresponding to the $^{99m}$Tc-PEG$_{4.25}$-IMMU-14-Fab shifted retention time to a higher molecular weight once it was bound to CEA, indicating that essentially all the antibody was bound to the CEA and that the PEG conjugate retained immunoreactivity upon $^{99m}$Tc labeling.

Example 5

Biodistribution of $^{99m}$Tc-PEG$_{4.25}$-IMMU-14-Fab following injection into experimental animals.

An experiment was performed to compare the kidney uptake of $^{99m}$Tc labeled IMMU-14-Fab-S H and PEG$_{4.25}$-IMMU-14-Fab-SH. Two groups of normal Balb/C mice were injected intravenously with 100 µCi of $^{99m}$Tc-labeled IMMU-14-Fab-SH (Group 1) or PEG$_{4.25}$-IMMU-14-Fab-SH (Group 2) per animal. Five mice from each group were sacrificed at 1, 4 and 24 h post injection. The tissues were removed, weighed and counted in a gamma counter. The % injected dose/g are shown in Table 2.

TABLE 2

Biodistribution at 1, 4 and 24 hours post-injection of $^{99m}$Tc-IMMU-14-Fab (Group 1) and $^{99m}$Tc PEG$_{4,25}$-IMMU-14-Fab (Group 2) into normal Balb/C mice.

| Tissue | time (h) post injection | % Injected dose/g tissue S.D. Group 1 | Group 2 |
|---|---|---|---|
| Liver | 1 | 10.33 ± 0.78 | 7.00 ± 0.31 |
|  | 4 | 8.82 ± 3.09 | 4.93 ± 2.10 |
|  | 24 | 3.17 ± 0.32 | 2.76 ± 0.37 |
| Spleen | 1 | 5.78 ± 0.21 | 5.14 ± 0.43 |
|  | 4 | 5.27 ± 1.57 | 3.76 ± 1.52 |
|  | 24 | 2.62 ± 0.27 | 2.52 ± 0.58 |
| L. kidney | 1 | 234.48 ± 21.33 | 29.63 ± 1.63 |
|  | 4 | 183.67 ± 80.67 | 43.27 ± 29.13 |
|  | 24 | 84.20 ± 6.38 | 10.76 ± 1.24 |
| Lungs | 1 | 13.45 ± 2.67 | 9.24 ± 0.87 |
|  | 4 | 7.20 ± 3.84 | 5.34 ± 1.37 |
|  | 24 | 1.91 ± 0.37 | 2.82 ± 0.27 |
| Blood | 1 | 10.66 ± 2.05 | 24.48 ± 0.96 |
|  | 4 | 4.00 ± 0.31 | 16.11 ± 1.80 |
|  | 24 | 0.78 ± 0.12 | 5.28 ± 0.72 |
| Stomach | 1 | 5.89 ± 1.61 | 3.94 ± 0.82 |
|  | 4 | 3.37 ± 1.99 | 1.81 ± 1.14 |
|  | 24 | 0.49 ± 0.25 | 0.60 ± 0.23 |
| S. intestine | 1 | 6.69 ± 1.31 | 3.68 ± 0.46 |
|  | 4 | 4.30 ± 1.82 | 2.20 ± 1.03 |
|  | 24 | 0.43 ± 0.07 | 0.68 ± 0.07 |
| L. intestine | 1 | 3.32 ± 0.66 | 1.77 ± 0.19 |
|  | 4 | 9.85 ± 3.56 | 4.33 ± 1.36 |
|  | 24 | 1.29 ± 0.52 | 0.95 ± 0.15 |

Example 6

Alternative Procedure for PEG Conjugation at higher pH and temperature.

The pH of IMMU-14-F(ab)$_2$ in 0.1M sodium phosphate pH 8.2 was raised to 8.58 with saturated tribasic sodium phosphate. To 221 µl of this solution (3.52 mg IMMU-14F (ab), 3.52×10$^{-8}$ mol), was added 5.8 µl of 0.1M sodium phosphate buffer, pH 8.2, and 17.6 µl (3.52×10$^{-7}$ mol) of a solution of methoxy-SC-PEG (0.1 mg/ml in pH 8.2 buffer). The reaction mixture was incubated at 25° C., pH 8.4, for 30 min. At the end of 30 min, the pH was 8.2 and HPLC analysis showed 2% unmodified F(ab)$_2$ which was modifiable upon adjustment of pH to 8.6 and further incubation at 25° C. for an additional 30 min.

Conjugation using 8, 6, or 4 fold molar excess of SC-PEG to IMMU-14-F(ab)$_2$ was performed at pH 8.5 for 30 min at 25° C. HPLC analysis showed complete modification at 30 min for 8 and 6 fold molar excess of SC-PEG, while the 4:1 molar ratio showed a small amount of unmodified F(ab)$_2$.

Example 7

Conjugation of Hz-PEG (methoxy polyethylene glycol hydrazide) to F(ab')$_2$ light chain carbohydrate.

LL2 is a murine monoclonal antibody that has been shown to be effective for the diagnosis and treatment of non-Hodgkins B-cell lymphoma. It is glycosylated in the light chain region and thus provides a specific site for PEG attachment in addition to the lysine residues.

Conjugation protocol (a).

IMMU-LL2-F(ab')$_2$ carbohydrate moiety was oxidized with sodium periodate (20 mM final concentration) at pH 6 for 90 min at 0° C. The oxidized fragment was separated from excess periodate by centrifuged spin-column technique, Sephadex G-50-80 in PBS pH 6.0. The hydrazone linkage was obtained through addition of methoxy-PEG hydrazide (MW 5000, Shearwater Polymers, Inc., Huntsville, Ala.) in molar excess (50× and 300×) to the purified oxidized intermediate. The reaction was allowed to proceed for two hours at room temperature. The products were purified with a centrifuged spin-column, containing Sephadex G-50-80, 0.1M sodium phosphate pH 7 and analyzed by size-exclusion HPLC using a BioSil SEC-400 column eluting with 0.2M sodium phosphate, 0.02% sodium azide, pH 6.8.

The results showed 16% unmodified for the reaction with 50× molar excess and only 2.3% unmodified F(ab')$_2$ for the reaction with 300× molar excess of Hz-PEG.

Conjugation protocol (b).

IMMU-LL2 F(ab)$_2$, 200 µl (2.1 mg, 2.1×10$^{-8}$ mol) was oxidized with 29.4 µl of 0.5M NaIO$_4$, (700×2.1×10$^{-8}$ mol) for 45 min at 26° C. The oxidized fragment was separated from excess NaIO$_4$ on two consecutive 2.4 ml centrifuged spin columns, Sephadex G-50-80 in 0.1M sodium phosphate, pH 7.

Conjugation of methoxy-Hz-PEG to the oxidized fragment was accomplished by incubating 205 µl (1.52 mg, 1.52×10$^{-8}$ mol) of oxidized IMMU-LL2F(ab)$_2$ with 22.8 mg (300×1.52×10$^{-8}$ mol) of methoxy-Hz-PEG(MW 5000) at 25° C. for 1 hr. The conjugate was purified on spin-column (4 consecutive 2.4 ml) of Sephadex-G-50-80, eluted with 0.1M sodium phosphate, pH 7. HPLC analyses on a size-exclusion column of BioSil 400 eluted with 0.2M sodium phosphate, 0.15M sodium chloride, 0.02% sodium azide pH 6.8, showed two new peaks, at 7.4 (16.9%) and 8.3 min (83.1%).

Example 8

Reduction of PEG-IMMU-LL2 F(ab)$_2$ to PEG-Fab.

Hz-PEG-IMMU-LL2F(ab)$_2$ (130 µl, 923 µg, 9.23×10$^{-9}$ mol) was reduced with 2.7 µl of 50 mM DTT and 2.7 µl of 0.1M EDTA by incubating at 37° C. for 30 min under argon. The reduced material was purified on two consecutive spin-columns, 1 ml, using Sephadex G-50-80 in 50 mM acetate, 150 mM sodium chloride, pH 5.3. Ellman analysis showed 4.8 thiol groups per Fab fragment. Size-exclusion HPLC analysis of the reduced species showed unresolved shoulders on the major peak at 9.31 min. A small amount of unmodified IMMU-LL2-Fab-SH was also observed.

Example 9

Formulation and $^{99m}$Tc Labeling of Hz-PEG-IMMU-LL2 F(ab)SH.

Hz-PEG-IMMU-LL2 Fab-SH was formulated in 200 µg amounts with 33 µg of Sn(II) with 6.5 fold molar excess of tartrate to tin. Sucrose (10% of final volume) was added before lyophilization.

The lyophilized vial was reconstituted with 3.5 mCi of sodium pertechnetate in 1 ml of argon-purged saline. The technetium-labeled vial was analyzed 5 min post-labeling on a size-exclusion HPLC column (BioSil 400) and also by ITLC. HPLC analysis showed the main broad peak at 9.78 min with unresolved shoulders. There was 3% unreduced sodium pertechnetate at retention time 12.67 min. For comparison, the retention time of technetium-labeled unmodified IMMU-LL2 Fab'-SH was 10.38 min.

Example 10

Diagnostic Imaging of Lymphoma using Hz-PEG-IMMU-LL2 F(ab)SH.

A patient presenting with a histologically-proven follicular, nodular, intermediate grade large cell lymphoma is injected with 1 mg (~25 mCi) of IMMU-LL2 F(ab)S-$^{99m}$Tc in saline solution. Multiple planar views of the abdomen and pelvis are taken using a Sopha DSX gamma-camera after 1,4 and 24 h. One week later the same patient is injected with Hz-PEG-IMMU-LL2 F(ab)S-$^{99m}$Tc, and the same imaging protocol is followed. A large abdominal lesion is clearly visible at 4 hours in the results obtained with the PEG conjugate, whereas in the 4 hour image using the non-conjugated antibody, that lesion is obscured by background radiation from the kidneys.

The invention has been disclosed broadly and illustrated in reference to representative embodiments described above. Those skilled in the art will recognize that various modifications can be made to the present invention without departing from the spirit and scope thereof.

What is claimed is:

1. In a method of imaging a tumor or infectious lesion, wherein a Tc-99m-radiolabeled antibody fragment that specifically binds a marker produced by or associated with a tumor or infectious lesion is injected parenterally into a patient having a tumor or infectious lesion, and the site or sites of tumor or infectious lesion are detected by external gamma camera imaging, the improvement wherein, prior to labeling with Tc-99m, said radiolabeled antibody fragment is conjugated to an amount of polyethylene glycol (PEG) sufficient to significantly reduce renal uptake and retention of the radiolabel compared to non-PEGylated antibody fragment.

2. The method of claim 1, wherein said antibody fragment is a divalent fragment.

3. The method of claim 1, wherein said antibody fragment is a monovalent fragment.

4. The method of claim 2, wherein about 2–20 PEG-5,000 moieties are conjugated to said divalent fragment.

5. The method of claim 3, wherein about 1–10 PEG-5,000 moieties are conjugated to said monovalent fragment.

6. The method of claim 1, wherein said PEG moieties are non-site-specifically conjugated to lysine residues on said antibody fragment.

7. A method of preparing an imaging agent precursor for eventual labeling with Tc-99m, comprising the steps of:

a) reacting a F(ab)$_2$ or F(ab')$_2$ antibody fragment that specifically binds a marker produced by or associated with a tumor or infectious lesion with an activated polyethylene glycol to form PEG-F(ab)$_2$ or PEG-F(ab')$_2$; and b) cleaving the PEG-F(ab)$_2$ or PEG-F(ab')$_2$ with a disulfide reducing agent to form PEG-Fab-SH or PEG-Fab'-SH, for eventual labeling with Tc-99m.

8. The method of claim 7, which further comprises adding stannous ions to the PEG-Fab-SH or PEG-Fab'-SH, in an amount effective for reducing 99m-pertechnetate, the 99m-pertechnetate to be added subsequently.

9. The method of claim 8, which further comprises the step of adding an effective imaging amount of 99m-pertechnetate to the mixture of stannous ions and PEG-Fab-SH or PEG-Fab'-SH, whereupon the 99m-pertechnetate is reduced to Tc-99m cations, which bind to the thiol groups of the PEG-Fab-SH or PEG-Fab'-SH, to form PEG-Fab-S-Tc-99m or PEG-Fab'-S-Tc-99m.

10. The method of claim 7, which further comprises adding reduced 99m-pertechnetate to the PEG-Fab-SH or PEG-Fab'-SH, to form PEG-Fab-S-Tc-99m or PEG-Fab'-S-Tc-99m.

11. A method of preparing an imaging agent precursor for eventual labeling with Tc-99m, comprising the steps of:

a) reacting a F(ab)$_2$ or F(ab')$_2$ antibody fragment that specifically binds a marker produced by or associated with a tumor or infectious lesion with an activated polyethylene glycol to form PEG-F(ab)$_2$ or PEG-F(ab')$_2$; and b) thiolating said PEG-F(ab)$_2$ or PEG-F(ab')$_2$ to form PEG-F(ab)$_2$-SH or PEG-F(ab')$_2$-SH, for eventual labeling with Tc-99m.

12. The method of claim 11, which further comprises adding stannous ions to the PEG-F(ab)$_2$-SH or PEG-F(ab')$_2$-SH, in an amount effective for reducing 99m-pertechnetate, the 99m-pertechnetate to be added subsequently.

13. The method of claim 12, which further comprises the step of adding an effective imaging amount of 99m-pertechnetate to the mixture of stannous ions and PEG-F(ab)$_2$-SH or PEG-F(ab')$_2$-SH, whereupon the 99m-pertechnetate is reduced to Tc-99m cations, which bind to the thiol groups of the PEG-F(ab)$_2$-SH or PEG-F(ab')$_2$-SH, to form PEG-F(ab)$_2$-S-Tc-99m or PEG-F(ab')$_2$-S-Tc-99m.

14. The method of claim 11, which further comprises adding reduced 99m-pertechnetate to the PEG-F(ab)$_2$-SH or PEG-F(ab')$_2$-SH, to form PEG-F(ab)$_2$-S-Tc-99m or PEG-F(ab')$_2$-S-Tc-99m.

15. A kit for use in preparing a Tc-99m-labeled imaging agent for a tumor or infectious lesion, comprising, in a single container:

an antibody fragment having at least one free thiol group, wherein said fragment specifically binds a marker produced by or associated with a tumor or infectious lesion, said fragment being conjugated to an amount of polyethylene glycol (PEG) sufficient to significantly reduce renal uptake and retention of the PEGylated antibody fragment after radiolabeling with Tc-99m, compared to non-PEGylated Tc-99m-labeled antibody fragment; and an amount of stannous ions effective for reducing 99m-pertechnetate, the 99m-pertechnetate to be added subsequently.

16. The kit of claim 15, wherein said fragment is a monovalent fragment conjugated to 1–10 PEG-5,000 moieties.

* * * * *